United States Patent
Cogan et al.

(10) Patent No.: US 10,450,557 B2
(45) Date of Patent: Oct. 22, 2019

(54) METHOD OF NUCLEIC ACID FRAGMENTATION

(71) Applicant: AGRICULTURE VICTORIA SERVICES PTY LTD, Atwood, Victoria (AU)

(72) Inventors: Noel Oliver Ian Cogan, Macleod (AU); Hiroshi Shinozuka, Kingsbury (AU)

(73) Assignee: Agriculture Victoria Services Pty Ltd, Attwood (AU)

( * ) Notice: Subject to any disclaimer, the term of this patent is extended or adjusted under 35 U.S.C. 154(b) by 773 days.

(21) Appl. No.: 14/716,212

(22) Filed: May 19, 2015

(65) Prior Publication Data

US 2015/0315571 A1    Nov. 5, 2015

Related U.S. Application Data

(63) Continuation of application No. PCT/AU2014/050193, filed on Aug. 20, 2014.

(51) Int. Cl.
    *C12N 15/10*    (2006.01)
    *C40B 50/06*    (2006.01)
    *C12Q 1/68*     (2018.01)
    *C12Q 1/6869*   (2018.01)
    *C12Q 1/6806*   (2018.01)

(52) U.S. Cl.
    CPC ......... *C12N 15/10* (2013.01); *C12N 15/1093* (2013.01); *C40B 50/06* (2013.01); *C12Q 1/6806* (2013.01); *C12Q 1/6869* (2013.01)

(58) Field of Classification Search
    None
    See application file for complete search history.

(56) References Cited

PUBLICATIONS

Miyazaki, "Random DNA fragmentation with endonuclease V: application to DNA shuffling," Nucleic Acids Res. 2002, 30(24):e139.*
Cohen-Karni et al., "The MspJI family of modification-dependent restriction endonucleases for epigenetic studies," Proc. Natl. Acad. Sci. USA 2011, 108(27):11040-11045.*
Huang, X. et al., High-throughput sequencing of methylated cytosine enriched by modification-dependent restriction endonuclease MspJI, BMC Genetics, 2013, (electonically available Jun. 18, 2013) pp. 1-9, vol. 14, Article 56.
Cohen-Karni, D. et al., The MspJI family of modification-dependent restriction endonucleases for epigenetic studies, Proceedings of the National Academy of Sciences,USA, 2011, pp. 11040-11045, vol. 108, No. 27.
Wang, H. et al., Comparative characterization of the PvuRts1I family of restriction enzymes and their application in mapping genomic 5-hydroxymethylcytosine, Nucleic Acids Research, 2011, pp. 9294-9305, vol. 39, No. 11.
Knierim, E. et al., Systematic Comparison of Three Methods for Fragmentation of Long-Range PCR Products for Next Generation Sequencing, PLoS ONE, 2011, vol. 6, No. 11, e28240, doi: 10.1371/journal.pone.00282402011.
Syed, F. et al., Optimized library preparation method for next-generation sequencing, Nature Methods, 2009, 6(10).
Syed, F. et al., Next-generation sequencing library preparation: simultaneous fragmentation and tagging using in vitro transposition, Nature Methods, 2009, 6(11).
Zheng, Y. et al.M, A unique family of Mrr-like modification-dependent restriction endonucleases, Nucleic Acids Research, 2010, pp. 5527-5534, vol. 38, No. 16, doi: 10.1093/nar/gkq327.
Hayden, H. L. et al., Changes in the microbial community structure of bacteria, archaea and fungi in response to elevated CO2 and warming in an Australian native grassland soil, Environmental Microbiology, 2012, pp. 3081-3096, vol. 14, No. 12, doi: 10.1111/j.1462-2920.2012.02855.x.
Written Opinion dated Sep. 30, 2014 from parent case International Patent Application No. PCT/AU2014/050193.
International Search Report dated Sep. 30, 2014 from parent case International Patent Application No. PCT/AU2014/050193.

* cited by examiner

*Primary Examiner* — Kaijiang Zhang
(74) *Attorney, Agent, or Firm* — Larson & Anderson, LLC

(57) ABSTRACT

A method of preparing an at least partially randomly sheared library of nucleic acids is provided. The method includes the steps of providing a source of nucleic acids, randomly incorporating modified bases into the nucleic acids, and digesting the modified nucleic acids with one or more modification-dependent restriction endonucleases to produce the nucleic acid library. The practice of the method can be facilitated using a kit for performing the method. The method can be used to form nucleic acid libraries and as part of a method of next generation sequencing.

9 Claims, 9 Drawing Sheets

Figures 1A, 1B:
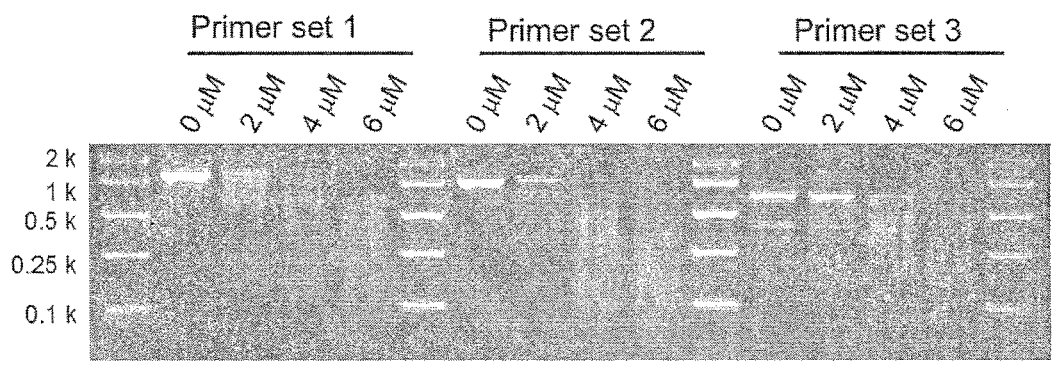

Specification includes a Sequence Listing.

Fig. 5A     a) 6 µM 5-methyl cytosine PCR amplicon-derived library
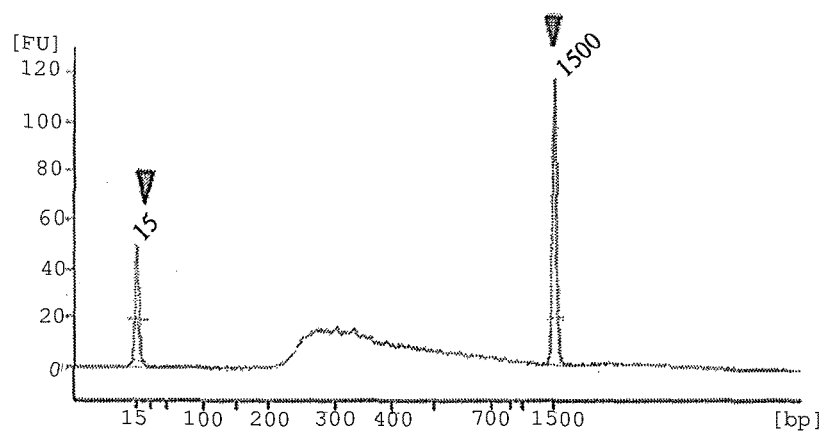
Fig. 5B     b) 8 µM 5-methyl cytosine PCR amplicon-derived library
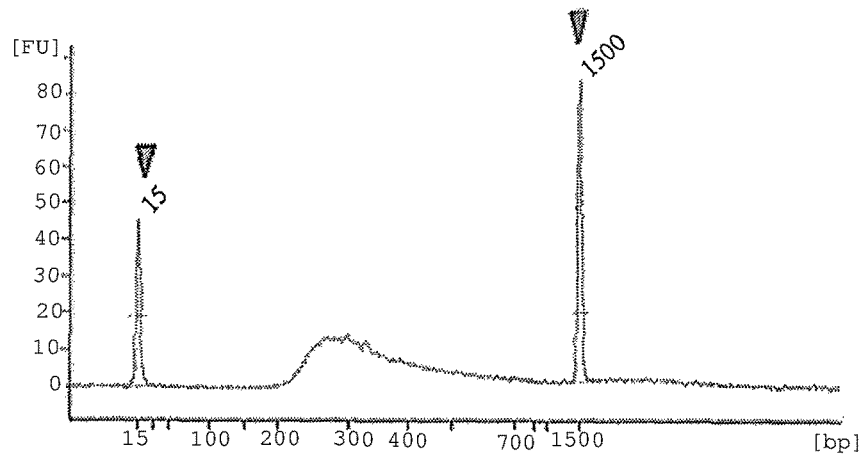
Fig. 5C     c) *Agrobacterium* genome-derived library
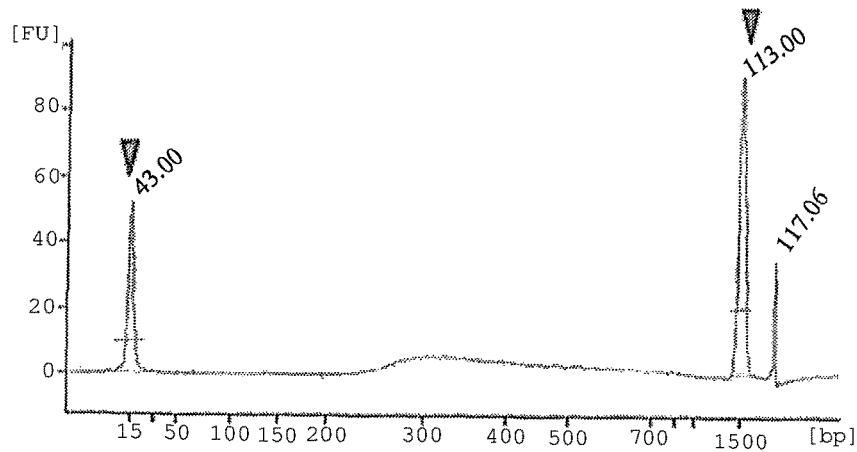

| Primer | Sequence (5'→3') |
|---|---|
| Set4_BtKIT1-10_f | CATGTAGTCATTCCTTCACTGTGC |
| Set4_BtKIT1-10_r | GTGGATAGATGGTAGAGACAGTTCC |
| Set5_BtKIT27-37_f | GGTTGAATAGGAGCTGGATTATGG |
| Set5_BtKIT27-37_r | GTACACATGTTACAACGCAGTCC | a) BtKIT1-10/MspJI library b) BtKIT1-10/FspEI library c) BtKIT1-10/LpnPI library d) BtKIT27-37/MspJI library e) BtKIT27-37/FspEI library f) BtKIT27-37/LpnPI library

METHOD OF NUCLEIC ACID FRAGMENTATION

FIELD OF THE INVENTION

The present invention relates to a method of nucleic acid fragmentation, more particularly semi-random enzymatic DNA fragmentation, and the use thereof in sequencing protocols including massively parallel sequencing or next generation sequencing, more particularly massively parallel short read sequencing.

BACKGROUND OF THE INVENTION

Randomised-nucleotide fragmentation is an essential process in DNA sequence library construction for the massively parallel short-read sequencing instruments (Knierim et al. 2011). The fragmentation permits generation of random read-initiation points in template nucleic acids. Sequence information of the template nucleic acids may be decoded through computational assembly of the short reads.

Physical shearing is generally recommended by the manufacturers of next-generation massively parallel DNA sequencing systems, due to reproducibility and randomness of fragmentation. For example, the Covaris system uses sound waves to fragment the nucleic acids. However, these systems are time consuming and expensive, and are likely to require the use of dedicated instruments.

The Nextera technology (Illumina) and NEBNext dsDNA Fragmentase kit (New England Biolabs) are alternative random DNA fragmentation methods that only require standard laboratory instruments (Syed et al. 2009a, Syed et al. 2009b; Knierim et al. 2011).

The Nextera technology uses a transposase and transposon complex for random fragmentation of template DNA and attachment of the appended transposon ends at the cleaved sites. The appended transposon end sequences permit PCR amplification and performance of sequencing reaction on the second-generation sequencing systems.

With the NEBNext dsDNA Fragmentase kit, double stranded template DNA is fragmented in two sequential steps; nicks are enzymatically introduced into double-stranded DNA and, the DNA is, then, cleaved at the nicked sites. These enzyme-based methods, however, require DNA sample preparation (buffer replacement and DNA concentration adjustment) for an effective digestion, and the size of generated fragments is sensitive to the DNA sample quality and reaction duration, all of which require optimisation for each sample in order to achieve the desired output.

MspJI is a recently characterized modification-dependent endonuclease (Zheng et al. 2010). This enzyme was identified from $Mycobacterium$ sp. JLS and recognizes CNNR (R=nucleotides G or A) sites, of which the first base is a 5-methylcytosine ($^m$C) or 5-hydroxymethylcytosine, cleaving DNA at $N_{12}/N_{16}$ bases away from the modified cytosine on the 3' side. Enzyme activity can be enhanced with the addition of a short double stranded DNA molecule including the MspJI recognition site (enzyme activator), but of insufficient length to be digested. Digestion of a range of genomic DNAs with the MspJI enzyme typically generates 32 to 34 bp fragments, which contain $^m$CpG or $^m$CNG sites central to the fragment. However, to date, this endonuclease has generally been used for detecting methylcytosine bases, detecting changes in methylation status of nucleic acids or assembling nucleic acids. For example, the methylation status of human genome has been analysed through sequencing of the 32 to 34 bp fragments (Cohen-Karni et al. 2012).

It is an object of the present invention to overcome, or at least alleviate, one or more of the difficulties or deficiencies associated with the prior art.

SUMMARY OF THE INVENTION

Accordingly, in a first aspect of the present invention, there is provided a method of preparing an at least partially randomly sheared library of nucleic acids, said method including:
providing a source of nucleic acids;
randomly incorporating modified bases into the nucleic acids; and
digesting the modified nucleic acids with one or more modification-dependent restriction endonucleases to produce the nucleic acid library.

BRIEF DESCRIPTION OF THE DRAWINGS/FIGURES

In the figures:

FIG. 1A. Sequence of locus specific PCR primers for the $Lolium\ perenne$ genome (SEQ ID NOs: 1-6).

FIG. 1B. MspJI-enzymatic digestion of DNA amplicons derived from PCRs containing 0, 2, 4 and 6 µM 5-methylcytosine.

Figure 2:
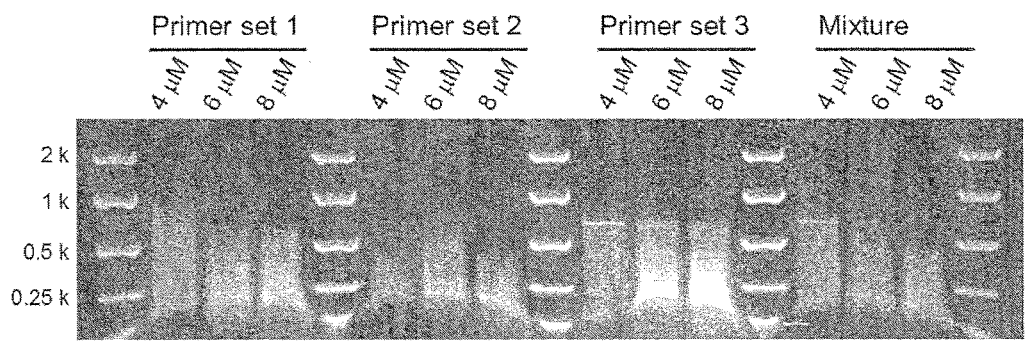

FIG. 2. MspJI-enzymatic digestion of DNA amplicons derived from PCRs containing 4, 6 and 8 µM 5-methylcytosine. Mixture denotes amplified DNA sample.

Figure 3:
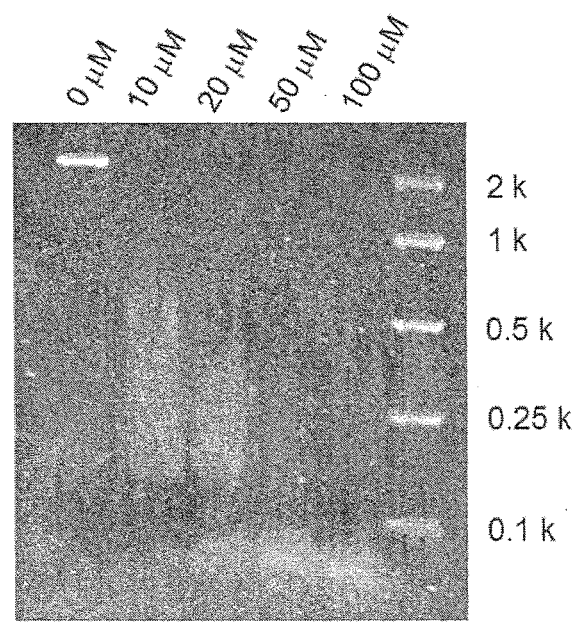

FIG. 3. MspJI-enzymatic digestion of ϕ29 enzyme-amplified DNA with randomly incorporated 5-methylcytosine from perennial ryegrass genomic DNA. 0, 10, 20, 50 and 100 µM denote final concentrations of 5-methylcytosine in the REPLI-g whole genome amplification mixture.

Figure 4:
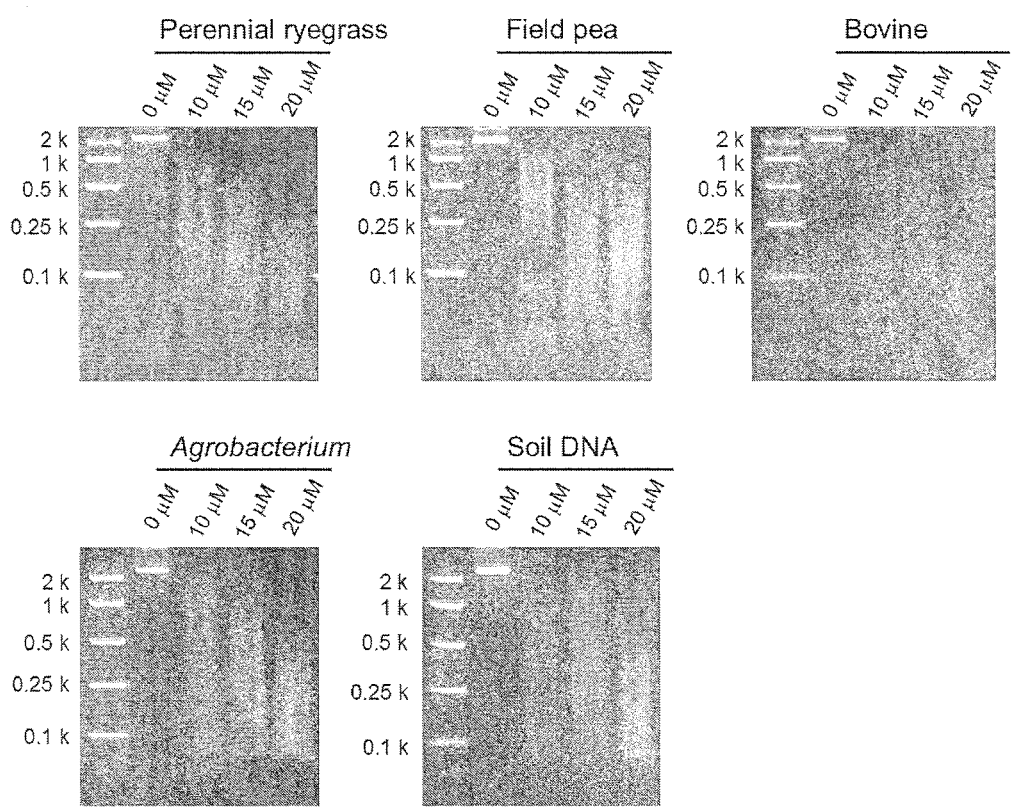

FIG. 4. MspJI-enzymatic digestion of 029-enzyme amplified DNA with randomly incorporated 5-methylcytosine from perennial ryegrass, field pea, bovine and $Agrobacterium$ genomic DNA and soil-extracted DNA. 0, 10, 15 and 20 µM denote final concentrations of 5-methylcytosine in the REPLI-g whole genome amplification mixture.

FIG. 5A-C. Illumina MiSeq sequencing libraries constructed with the MspJI-digested PCR amplicons and ϕ29-enzyme amplified DNA. Sharp peaks indicated by triangles show size standards (15 bp and 1,500 bp) of the Agilent DNA 1000 Kit. A peak between 200 and 1,500 bp represents size distribution of DNA fragments of the constructed DNA library.

Figure 6A:
Figure 6B:
Figure 6C:
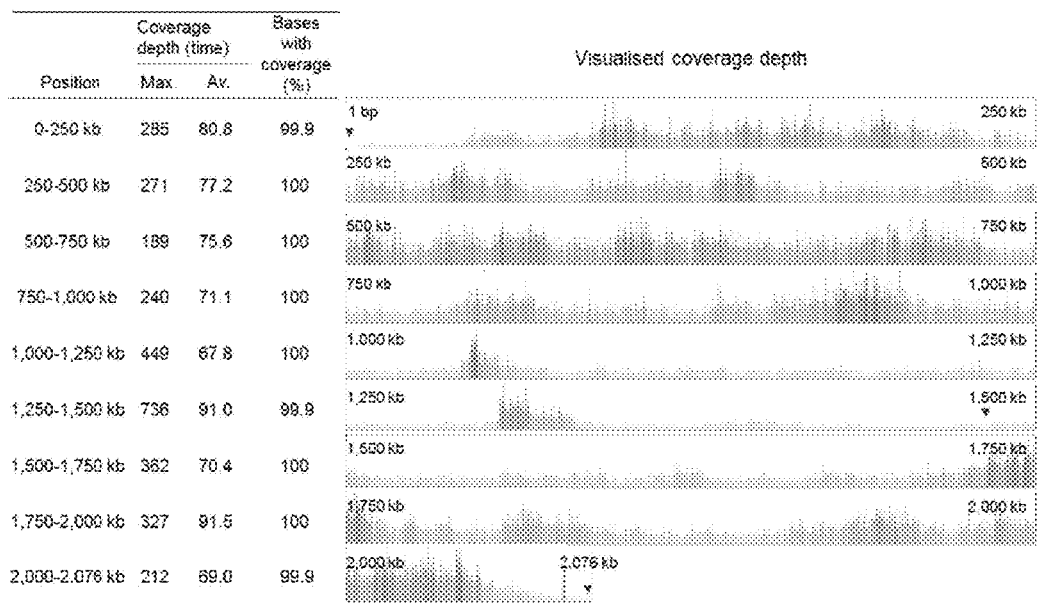

FIG. 6A-C. Illumina MiSeq short read-sequencing results of the libraries constructed from MspJI-digested DNA. Alignments were performed using the BWA software package and processed using SAMtools. The sorted alignment was visualised using the Tablet viewer. a) Alignment results of PCR amplicon-derived reads to the reference sequences and obtained maximum (max.) and average (av.) coverage depth. b) and c) Alignment results of $Agrobacterium$ genome-derived reads to the reference $Agrobacterium$ genome sequences and obtained maximum and average coverage depth for each 250 kb interval. The triangle indicates a position in the reference which was not resequenced.

Figures 7A, 7B:
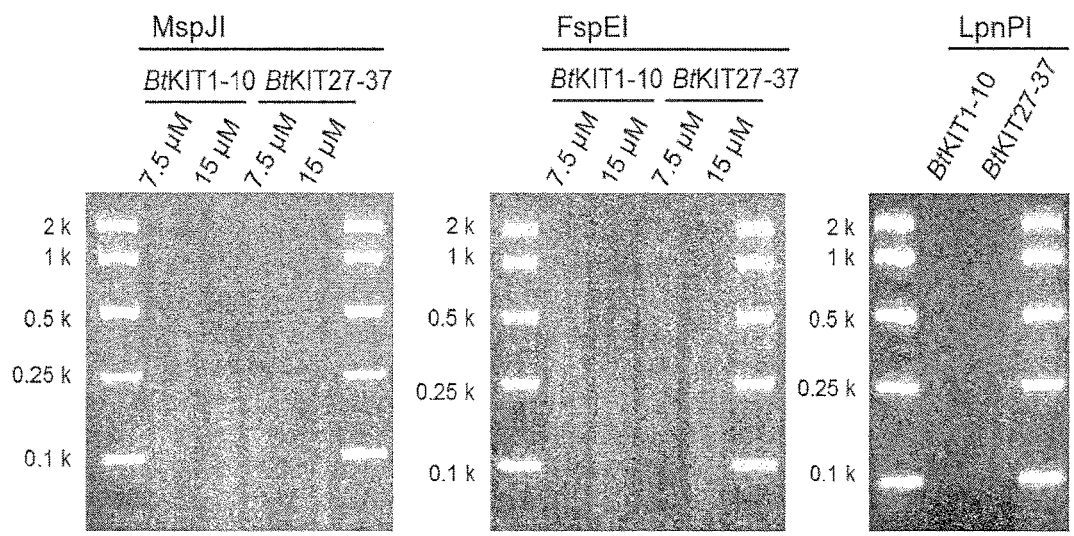
Figure 8A:
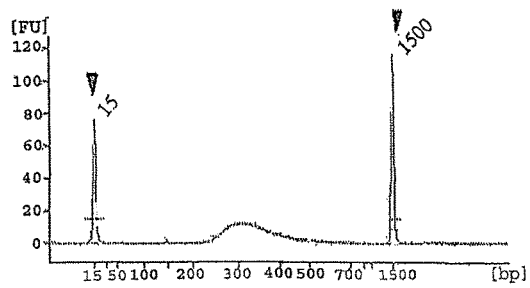
Figure 8B:
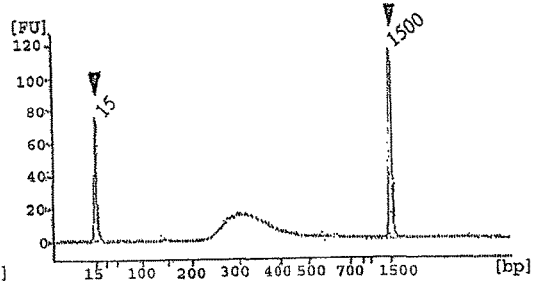
Figure 8C:
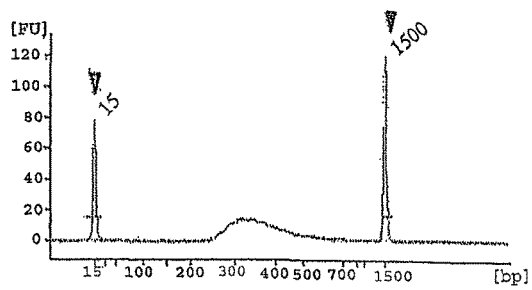
Figure 8D:
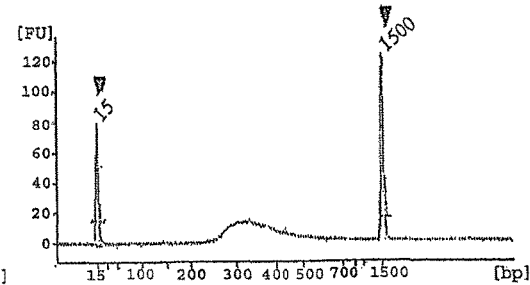
Figure 8E:
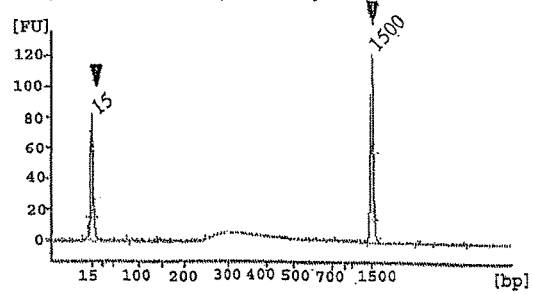
Figure 8F:
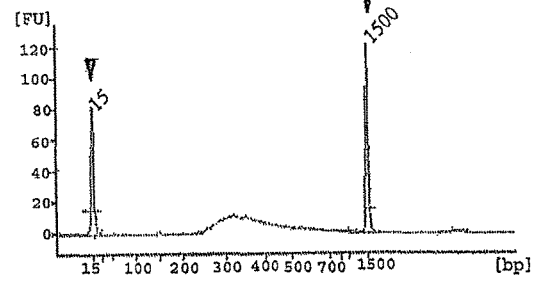

FIG. 7A. Primer sequences. (SEQ ID Nos: 7-10)

FIG. 7B. MspJI, FspEI and LpnPI-enzymatic digestion of DNA amplicons of BtKIT1-10 and BtKIT27-37 sequences derived from PCRs containing 7.5 and 15 (MspJI and FspEI) or 60 (LpnPI) µM 5-methylcytosine.

FIG. 8A-F. Illumina MiSeq sequencing libraries constructed with the MspJI, FspEI and LpnPI-digested PCR amplicons. Sharp peaks indicated by triangles show size standards (15 bp and 1,500 bp) of the Agilent DNA 1000 Kit. A peak between 200 and 1,500 bp represents size distribution of DNA fragments of the constructed DNA library.

Figure 9:
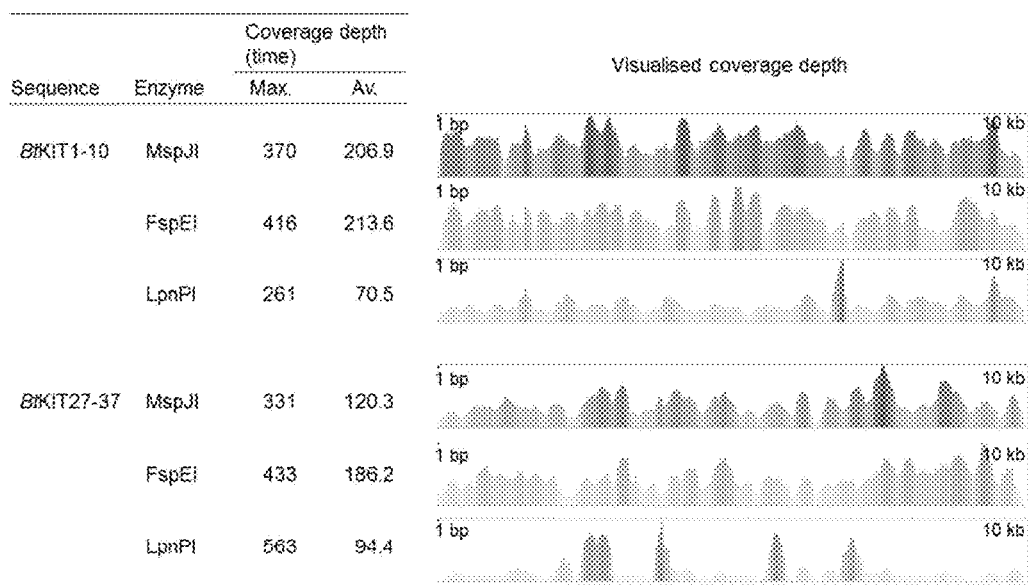

FIG. 9. Illumina MiSeq short read-sequencing results of the libraries constructed from MspJI, FspEI and LpnPI-digested DNA. Alignments were performed using the BWA software package and processed using SAMtools. The sorted alignment was visualised using the Tablet viewer and maximum (max.) and average (av.) coverage depth are shown.

DETAILED DESCRIPTION OF THE INVENTION

Applicants have found that the present method is particularly suitable for preparing nucleic acid libraries for sequencing, such as next-generation sequencing, and more particularly for use in massively parallel short read sequencing instruments or protocols.

By 'next-generation sequencing' or 'massively parallel sequencing', as used herein, is meant high-throughput sequencing where the sequencing process is performed in parallel, for example producing thousands or millions of sequences at once.

By 'at least partially randomly sheared' is meant that the nucleic acids are fragmented in a semi-random manner, wherein the cut sites are at least partially randomly distributed, resulting in a relatively even coverage of fragments across the genome to be sequenced.

The source of nucleic acids may be of any suitable type. For example, the source of nucleic acids may be genomic DNA from an organism of interest, such as a plant, fungus, microorganism, insect, animal or human.

By 'nucleic acid' is meant a chain of nucleotides capable of genetic information. The term generally refers to genes or functionally active fragments or variants thereof and or other sequences in the genome of the organism that influence its phenotype. The term 'nucleic acid' includes DNA (such as cDNA or genomic DNA) and RNA (such as mRNA or microRNA) that is single- or double stranded, optionally containing synthetic, non-natural or altered nucleotide bases, synthetic nucleic acids and combinations thereof.

The modified bases may be incorporated in any suitable manner, for example by amplifying the nucleic acids in the presence of modified bases. The amplification may be PCR amplification. In a preferred embodiment amplification of the nucleic acids may be performed with a DNA polymerase in the presence of a modified base such as modified cytosine.

By 'modified cytosine' is meant a cytosine molecule with modification on the pyrimidine ring, including 5-methylcytosine, 5-hydroxymethylcytosine, 5-formyl-cytosine and 5-carboxy-cytosine. In a particularly preferred embodiment, the modified cytosine may be 5-methylcytosine.

The method of the present invention may be used for generation of DNA fragments with randomly-incorporated modified cytosine bases, which may subsequently be converted into short DNA fragments via restriction enzymatic digestion based on the randomly-incorporated modified cytosine bases.

The method may enable control of the size range of fragmented DNA molecules through adjustment of the amount of modified bases incorporated into the nucleic acids, for example by adjusting the concentration of modified bases present during amplification of the nucleic acids. In a preferred embodiment, the nucleic acids may include a low-ratio of randomly-incorporated modified cytosine bases compared with non-modified cytosine bases, for example approximately 0.1% to 30%, more preferably approximately 0.5% to 5%, even more preferably approximately 1% to 4% (which corresponds to approximately 2 µM to 8 µM modified cytosine bases).

By a nucleic acid 'library', as used herein, is meant is a collection of nucleic acid molecules. In this context the nucleic acid library is preferably an at least partially randomly sheared library of nucleic acids, where the representation of individual nucleic acid molecules in the library is semi random.

The modified nucleic acids may be digested with one or more modification-dependent restriction endonucleases to generate short nucleic acid fragments via restriction enzymatic digestion of the nucleic acids at or near recognition sites with randomly-incorporated modified cytosine bases. In a preferred embodiment, the digestion may produce a library of nucleic acid fragments where the majority of the fragments are in the size range of approximately 10 to 3000 bases, more preferably approximately 20 to 2500 bases, even more preferably approximately 30 to 2000 bases, even more preferably approximately 40 to 1000 bases, even more preferably 50 to 500 bases, even more preferably approximately 100 to 400 bases. A particularly preferred size range is approximately 200 to 250 bases.

By 'the majority of the fragments' is meant at least approximately 50% of the fragments, preferably at least approximately 80% of the fragments, more preferably at least approximately 90% of the fragments, even more preferably at least approximately 95% of the fragments, even more preferably at least approximately 98% of the fragments.

By a 'modification-dependent restriction endonuclease' is meant a restriction endonuclease that cleaves the nucleic acid at or near a recognition site that includes the modified base. In a preferred embodiment, the recognition site may include at least one redundant base. For example, one or more of the bases in the recognition site may be selected from the group consisting of N (any nucleotide), R (A or G), Y (C or T), D (A, G or T) and H (A, C or T). This sort of 'loose' recognition site facilitates shearing by the restriction endonuclease in a semi-random manner.

A particularly preferred restriction endonuclease is the MspJI restriction enzyme. This is a DNA modification-dependent restriction endonuclease which is a distant homologue of *Escherichia coli*'s Mrr. The MspJI enzyme recognizes $^m$CNNR sequence of double stranded DNA, of which the $^m$C base stands for 5-methylcytosine or 5-hydroxymethylcytosine. It cleaves DNA at a fixed distance away from the recognition site, for example 12 or 16 bases away from the modified cytosine on the 3' side.

MspJI belongs to a family of modification dependent restriction endonucleases, any of which may be used in the method of the present invention. For example, one or more of the enzymes MspJI, LpnPI, FspEI, AspBHI, RlaI and SgrTI may also be used in the method of the present invention. LpnPI and FspEI are also preferred.

The nucleic acid library so generated may be suitable for sequencing utilising techniques such as next-generation sequencing. In a preferred embodiment, the nucleic acid library may be a DNA sequencing library suitable for use in massively parallel short read sequencing instruments.

By a 'DNA sequencing library' is meant a pool of relatively short DNA fragments suitable for sequencing, for example using massively parallel short read sequencing technology. The DNA fragments may be attached with adaptor sequence(s) at fragment terminus/termini, permitting initiation of the sequencing reaction.

In a further aspect of the present invention, there is provided an at least partially randomly sheared library of nucleic acids produced by the method of the present invention.

Preferably, the library of nucleic acids includes a majority of fragments in the size range of approximately 10 to 3000 bases, more preferably approximately 20 to 2500 bases, even more preferably approximately 30 to 2000 bases, even more preferably approximately 40 to 1000 bases, even more preferably 50 to 500 bases, even more preferably approximately 100 to 400 bases. A particularly preferred size range is approximately 200 to 250 bases.

By 'a majority of fragments' is meant at least approximately 50% of the fragments, preferably at least approximately 80% of the fragments, more preferably at least approximately 90% of the fragments, even more preferably at least approximately 95% of the fragments, even more preferably at least approximately 98% of the fragments.

In a still further aspect of the present invention, there is provided a method of next generation sequencing including sequencing an at least partially randomly sheared library of nucleic acids produced by the method of the present invention.

In a still further aspect of the present invention, there is provided a kit including one or more modification-dependent restriction endonucleases together with instructions for preparing an at least partially randomly sheared library of nucleic acids by the method of the present invention.

Preferably the modification-dependent restriction endonuclease cleaves the nucleic acids at or near a recognition site that includes a modified base, as hereinbefore described. In a preferred embodiment, the recognition site may include at least one redundant base. For example, one or more of the bases in the recognition site may be selected from the group consisting of N (any nucleotide), R (A or G), Y (C or T), D (A, G or T) and H (A, C or T).

In a preferred embodiment, the kit includes one or more restriction endonucleases selected from the group consisting of MspJI, LpnPI, FspEI, AspBHI, RlaI and SgrTI, as hereinbefore described. The enzymes MspJI, LpnPI and FspEI are particularly preferred.

In a preferred embodiment, the kit further includes a modified base. Preferably the modified base is a modified cytosine including, for example, 5-methylcytosine, 5-hydroxymethylcytosine, 5-formyl-cytosine or 5-carboxy-cytosine. In a particularly preferred embodiment, the modified cytosine may be 5-methylcytosine.

In another preferred embodiment, the kit further includes a DNA polymerase.

The kit may further include other components, including but not limited to buffers such as PCR buffers, primers such as forward and/or reverse primers for PCR, nucleotides such as dNTPs, salt solutions such as $MgSO_4$, solvents, diluents, and other components for amplifying, purifying and/or digesting nucleic acids.

As used herein, except where the context requires otherwise, the term "comprise" and variations of the term, such as "comprising", "comprises" and "comprised", are not intended to exclude further additives, components, integers or steps.

As used herein, except where the context requires otherwise, the singular forms "a", "an" and "the" include plural aspects.

The present invention will now be more fully described with reference to the accompanying examples and figures. It should be understood, however, that the description following is illustrative only and should not be taken in any way as a restriction on the generality of the invention description above.

EXAMPLES

Four experiments were performed to demonstrate applicability of the protocol. (1) Amplification of c. 650-1200 bp fragments using a modified amplification protocol followed by digestion. (2) Extraction of genomic DNA from a range of organisms, followed by whole genome amplification and then digestion. (3) Amplification of a bacterial genome DNA sample, followed by digestion and Illumina-based TrueSeq sample processing and sequencing. (4) Demonstration of the protocol's applicability with a range of related restriction enzymes to MspJI (e.g. FpEI or LpnPI based on long amplicon digestion and sequencing.

Example 1—Generation and MspJI-Enzymatic Digestion of DNA Fragments with Modified Cytosine Randomly Incorporated Through PCR Using a Range of Polymerases PCR amplification was performed with a standard DNA polymerase that lacks 3'→5' exonuclease activities [Immolase™ DNA polymerase (BIOLINE)] and 5-methylcytosine (TriLink). Perennial ryegrass (*Lolium perenne* L.) genomic DNA was used as DNA template and locus-specific oligonucleotide primers were prepared. The PCR mixture consisted of 0.5 ng/μl DNA template, 1×PCR buffer, 200 μM dNTP, 0.5 μM forward primer, 0.5 μM reverse primer, 0.05 U/μl Immolase™ DNA polymerase and 2, 4 or 6 μM 5-methylcytosine. The 4, 6 and 8 μM concentrations of 5-methylcytosine correspond to 1, 2 and 3% concentrations, respectively, compared with non-modified cytosine (percentage of 5-methylcytosine/non-modified cytosine). The PCR conditions consisted of 30 cycles of denaturation (95° C. for 30 seconds), annealing (60° C. for 30 seconds) and extension (72° C. for 1 minute), following enzyme activation (95° C. for 10 minutes). The amplified DNA (5 μl) was digested with the MspJI restriction enzyme (3 U) following the manufacture's protocol. After incubation at 37° C. for 4 hours, the MspJI restriction enzyme was heat-inactivated at 70° C. for 20 minutes. The digested DNA was then visualised on a 2.5% (w/v) agarose gel stained with SYBR® Safe (Life Technologies) (FIG. 1).

PCR amplification was performed with a high fidelity polymerase with 3'→5' exonuclease activities [KOD hot start DNA polymerase (TOYOBO)] and 5-methylcytosine (TriLink). Perennial ryegrass genomic DNA was used as the DNA template and then locus specific-oligonucleotide primers were used. The PCR mixture consisted of 2 ng/μl DNA template, 1×PCR buffer, 1 mM $MgSO_4$, 200 μM dNTP, 0.3 μM forward primer, 0.3 μM reverse primer, 0.02 U/μl KOD hot start DNA polymerase and 4, 6 or 8 μM 5-methylcytosine. The 4, 6 and 8 μM concentrations of 5-methylcytosine correspond to 2, 3 and 4% concentrations, respectively, compared with non-modified cytosine. The PCR cycling conditions consisted of 30 repeats of denaturation (95° C. for 20 seconds), annealing (60° C. for 10 seconds) and extension (70° C. for 15 seconds), following enzyme activation (95° C. for 2 minutes). The amplified DNA (5 μl) was digested with the MspJI restriction enzyme (3 U) following the manufacture's protocol. After incubation at 37° C. for 4 hours, the MspJI restriction enzyme was heat-inactivated at 70° C. for 20 minutes. The digested DNA was then visualised on a 1.5% (w/v) agarose gel stained with SYBR® Safe (Life Technologies) (FIG. 2).

Example 2—Generation and MspJI-Enzymatic Digestion of DNA Fragments with Modified Cytosine Randomly Incorporated Through φ29 Enzyme Whole Genome Amplification Whole genomic DNA amplification was performed using the φ29 enzyme contained within the REPLI-g kit (QIAGEN) and 5-methylcytosine (TriLink). Genomic DNA samples from perennial ryegrass were used as the DNA template. Following the manufacturer's protocol, 2.5 µl DNA (12.5 ng) was denatured with the D1 solution for three minutes, and then neutralized with the N1 solution. The amplification was performed in the reaction mixture with the addition of 10, 20, 50 and 100 µM 5-methylcytosine at 30° C. for 16 hours. After the incubation, DNA polymerase was heat-inactivated, and the products were diluted with an equal amount of water. The amplified DNA was digested with the MspJI restriction enzyme (3 U) following the manufacture's protocol. After incubation at 37° C. for 4 hours, the MspJI restriction enzyme was heat-inactivated at 70° C. for 20 minutes. The digested DNA was then visualised on a 2.5% (w/v) agarose gel stained with SYBR® Safe (Life Technologies) (FIG. 3).

Following initial assessment of the optimal concentration of 5-methylcytosine to add to the genomic amplification an expanded selection of templates was assembled. Genomic DNA from perennial ryegrass, field pea (*Pisum sativum* L. subsp. *sativum* var. arvense (L.) Poir.), bovine (*Bos Taurus*), and *Agrobacterium tumefaciens*, and a DNA sample extracted from soil harvested in South Australia (Soil DNA) were used as DNA templates. The DNA templates were prepared using the QIAGEN DNeasy kit (QIAGEN) (perennial ryegrass and field pea), PUREGENE® DNA Purification Kit (Gentra) (bovine), BioRad AquaPure Genomic DNA Kit (BioRad) (*Agrobacterium*) and MoBio Powersoil kit (MoBio) with modifications (Soil DNA) (Hayden et al. 2012). Sub-optimal digestion of the initial perennial ryegrass sample was determined to have occurred at concentrations of 5-methylcytosine that were greater than 20 nM. Following the manufacturer's protocol, 2.5 µl DNA (concentration ranging from 12.5-75 ng) was denatured with the D1 solution for three minutes, and then, neutralized with the N1 solution. The amplification was performed in the reaction mixture with the addition of 10, 15 or 20 µM 5-methylcytosine at 30° C. for 16 hours. After the incubation, the DNA polymerase was heat-inactivated, and the products were diluted with an equal amount of water. The amplified DNA was digested with the MspJI restriction enzyme (3 U) following the manufacture's protocol. After incubation at 37° C. for 4 hours, the MspJI restriction enzyme was heat-inactivated at 70° C. for 20 minutes. The digested DNA was then visualised on a 2.5% (w/v) agarose gel stained with SYBR® Safe (Life Technologies) (FIG. 4).

DNA fragmentation occurred in all of the different DNA samples. At a concentration of 20 µM, the generated size distribution of fragments varies across the different samples, with all samples producing fragments that were visualised as <100 bp on the agarose gel. However, the maximum of the range was identified as c. 250 bp (bovine) to c. 2,000 bp (field pea).

Example 3—Construction of DNA Sequencing Libraries for the Illumina MiSeq Platform with the MspJI-Digested PCR Amplicons and φ29 Enzyme-Amplified DNA The DNA sequencing library was constructed using the MspJI-digested DNA fragments (6 and 8 µM of 5-methylcytosine sample of PCR amplicons, and the 15 nM 5-methylcytosine sample of the *Agrobacterium* strain). Pre-activated KOD polymerase (0.2 U) was added to the *Agrobacterium* strain-derived MspJI-digested products (10 µl), and the mixture was incubated at 70° C. for 20 minutes for end-filling and blunt-ending of the DNA fragments with residual dNTPs. The blunt-end DNA was cleaned with the AMPure bead kit (Beckman Coulter) and used as the input for the adenine-tailing reaction step of the TruSeq DNA Sample Preparation kit (Illumina). The following procedures required and specified in the manufacture's protocol were performed. The resulting DNA libraries were quantified with the KAPA Library Quantification Kit (Kapa Biosystems) and validated with Agilent Technologies 2100 Bioanalyzer and Agilent DNA 1000 Kit (Agilent), following manufacture's protocols (FIG. 5).

DNA sequencing of the prepared library was performed using an Illumina MiSeq platform. A 2×150 bp read sequencing kit was used to generate sequence output. Reads were attributed to the samples by the use of sample-specific DNA bar codes. The generated sequence reads were then checked for quality and integrity using a custom PERL script. Any reads with greater than 3 consecutive Ns or more than 3 nucleotides with PHRED score ≤20 or a median PHRED score <20 or a read length <50 nucleotides were trimmed or removed. The specific DNA sequence reads were then reference aligned to the respective amplicon or *Agrobacterium* sequence. Reference alignments were performed using the BWA software package and then converted to a sorted BAM file using the SAMtools software package (samtools.sourceforge.net). The distribution of the generated fragments was examined using the sequencing output from the *Agrobacterium* strain, for which an appropriate reference genome sequence was available. Alignment of the sequencing reads to the reference sequences was visualised using the Tablet software, which was developed and distributed by the James Hutton Plant Bioinformatics Group (FIG. 6). Totals of 9,265 to 17,101 PCR reads derived from the PCR amplicons were aligned with each reference sequence, and totals of 1,380,029 and 1,219,389 reads were aligned with the *Agrobacterium* circular and linear chromosomes, respectively. All nucleotides of the reference sequences for the PCR amplicon were covered with the sequencing reads. Although 3 nucleotides of the *Agrobacterium* circular chromosome and a total of 137 nucleotides of the *Agrobacterium* linear chromosome were not covered with the sequencing reads, over 99.99% of nucleotides were aligned with the sequencing read. The alignment result indicated relatively random digestion of the input DNA with the MspJI-based shearing method.

Example 4—Construction of DNA Sequencing Libraries for the Illumina MiSeq Platform with MspJI, FspEI or LpnPI-Digested PCR Amplicons PCR amplification was performed with the Expand Long Range dNTPack (Roche Applied Science) and 5-methylcytosine (TriLink). Bovine (*Bos taurus* L.) genomic DNA was used as DNA template and locus-specific oligonucleotide primers were prepared. The PCR mixture consisted of 4 ng/μl DNA template, 1×PCR buffer, 500 μM dNTP, 0.3 μM forward primer, 0.3 μM reverse primer, 1×DNA polymerase and 7.5, 15 or 60 μM 5-methylcytosine. DNA amplicons from the 7.5, 15 or 60 μM 5-methylcytosine-including PCR solutions were digested with MspJI, FspEI or LpnPI (FIG. 7). A DNA sequencing library was constructed using the enzymatically-digested DNA fragments. Klenow Fragment (3'→5' exo⁻) (2 U; NEB) was added to MspJI-digested DNA, and the mixture was incubated at 37° C. for 30 minutes. Following ligation of the DNA adapter index with T4 DNA ligase (NEB), the ligated DNA was purified with the AMPure XP bead kit (Beckman Coulter) and enriched through PCR. The resulting DNA libraries were quantified with the KAPA Library Quantification Kit (Kapa Biosystems) and validated with Agilent Technologies 2100 Bioanalyzer and Agilent DNA 1000 Kit (Agilent), following manufacturer's protocols (FIG. 8).

DNA sequencing of the prepared library was performed using an Illumina MiSeq platform. A 2×250 bp read sequencing kit was used to generate sequence output. Reads were attributed to the samples by the use of sample-specific DNA bar codes. The generated sequence reads were then checked for quality and integrity using a custom PERL script. Any reads with greater than 3 consecutive Ns or more than 3 nucleotides with PHRED score ≤20 or a median PHRED score <20 or a read length <50 nucleotides were trimmed or removed. The specific DNA sequence reads were then reference aligned to the respective amplicon sequence. Reference alignments were performed using the BWA software package and then converted to a sorted BAM file using the SAMtools software package (samtools.sourceforge.net). Alignment of the sequencing reads to the reference sequences was visualised using the Tablet software (FIG. 9).

Totals of 3,566 to 10,972 reads were aligned with each reference sequence. All nucleotides of the reference sequences for the PCR amplicon were covered with the sequencing reads. CVs of read coverage for specific nucleotides was calculated to be between 0.29 and 1.11. The read alignment result indicated that the read distribution from the LpnPI-digested library was more skewed than those from the other libraries, and there was no substantial difference in the CVs between the MspJI- and FspEI-digested libraries.

REFERENCES

Cohen-Karni D, Xu D, Apone L, et al. (2011) The MspJI family of modification-dependent restriction endonucleases for epigenetic studies. Proceedings of the National Academy of Sciences 108:11040-11045. doi: 10.1073/pnas.1018448108

Hayden H L, Mele P M, Bougoure D S, et al. (2012) Changes in the microbial community structure of bacteria, archaea and fungi in response to elevated $CO_2$ and warming in an Australian native grassland soil. Environmental microbiology 14:3081-96. doi: 10.1111/j.1462-2920.2012.02855.x Knierim E, Lucke B, Schwarz J M, et al. (2011) Systematic Comparison of Three Methods for Fragmentation of Long-Range PCR Products for Next Generation Sequencing. PLoS ONE 6:e28240. doi: 10.1371/journal.pone.0028240

Syed F, Grunenwald H, Caruccio N (2009a) Optimized library preparation method for next-generation sequencing. Nature Methods 6(10)

Syed F, Haiying G, Nicholas C (2009b) Next-generation sequencing library preparation: simultaneous fragmentation and tagging using in vitro transposition. Nature Methods 6(11)

Zheng Y, Cohen-Karni D, Xu D, et al. (2010) A unique family of Mrr-like modification-dependent restriction endonucleases. Nucleic Acids Research 38:5527-5534. doi: 10.1093/nar/gkq327

The claims defining the invention are as follows:

1. A method of preparing an at least partially randomly sheared library of nucleic acids suitable for use in next generation sequencing, said method comprising:
   providing a source of nucleic acids;
   randomly incorporating modified bases into the nucleic acids, wherein said modified bases are modified cytosine bases; and
   digesting the modified nucleic acids with one or more modification-dependent restriction endonucleases to produce the nucleic acid library, said nucleic acid library being suitable for use in next generation sequencing.

2. The method according to claim 1, wherein the nucleic acid library contains nucleic acid fragments wherein the majority of the fragments are in the size range 50 to 500 bases.

3. The method according to claim 2, wherein the modified bases are incorporated into the nucleic acids by amplifying the nucleic acids in the presence of the modified bases.

4. The method according to claim 3, wherein the amplification is performed with DNA polymerase.

5. The method according to claim 1, wherein the modified cytosine bases are incorporated in a ratio of between approximately 0.5 to 5% modified cytosine bases to non-modified cytosine bases.

6. The method according to claim 5, wherein the modified cytosine base is 5-methylcytosine.

7. The method according to claim 1, wherein the modification-dependent restriction endonuclease has a recognition site that includes at least one redundant base.

8. The method according to claim 7, wherein the modification-dependent restriction endonuclease is selected from the group consisting of MspJI, LpnPI and FspEI.

9. A method of next generation sequencing, comprising:
   preparing an at least partially randomly sheared library of nucleic acids, said method comprising:
      providing a source of nucleic acids,
      randomly incorporating modified bases into the nucleic acids, wherein said modified bases are modified cytosine bases, and
      digesting the modified nucleic acids with one or more modification-dependent restriction endonucleases to produce the nucleic acid library, said nucleic acid library being suitable for use in next generation sequencing; and
   sequencing the at least partially randomly sheared library of nucleic acids.

* * * * *

```
                        SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
catctaatgg gagaggatct                                         20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
gagggtcgta gaaagtggaa                                         20

<210> SEQ ID NO 3
<211> LENGTH: 20
<212> TYPE: DNA
<213> ORGANISM: Artificial Sequence
<220> FEATURE:
<223> OTHER INFORMATION: Primer
```

<400> SEQUENCE: 3
gcatcccgtc cacatgatag                                          20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
accaatggag gtattctctg                                          20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gtgctctatc ccacgttgac                                          20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ggccccagtc tatcaagcga                                          20

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
catgtagtca ttccttcact gtgc                                     24

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
gtggatagat ggtagagaca gttcc                                    25

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
ggttgaatag gagctggatt atgg                                     24

<210> SEQ ID NO 10

```
<211> LENGTH: 23
<212> TYPE: DNA
<213> ORGANISM: Artificial Sequence
<220> FEATURE:
<223> OTHER INFORMATION: Primer

<400> SEQUENCE: 10
gtacacatgt tacaacgcag tcc                                              23
```